(12) United States Patent
Ishii et al.

(10) Patent No.: US 8,669,382 B2
(45) Date of Patent: Mar. 11, 2014

(54) METHOD FOR PRODUCING (2R)-2-FLUORO-2-C-METHYL-D-RIBONO-γ-LACTONE PRECURSOR

(75) Inventors: Akihiro Ishii, Kawagoe (JP); Hirokatsu Nagura, Kawagoe (JP); Hideyuki Tsuruta, Kawagoe (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

(21) Appl. No.: 13/697,691

(22) PCT Filed: Apr. 25, 2011

(86) PCT No.: PCT/JP2011/060024
§ 371 (c)(1),
(2), (4) Date: Nov. 13, 2012

(87) PCT Pub. No.: WO2011/152155
PCT Pub. Date: Dec. 8, 2011

(65) Prior Publication Data
US 2013/0072699 A1    Mar. 21, 2013

(30) Foreign Application Priority Data

Jun. 3, 2010 (JP) .................................. 2010-127561
Dec. 21, 2010 (JP) .................................. 2010-283922
Apr. 4, 2011 (JP) .................................. 2011-082364

(51) Int. Cl.
*C07D 317/10* (2006.01)

(52) U.S. Cl.
USPC ............................. 549/454; 549/429; 549/430

(58) Field of Classification Search
USPC ......................................... 549/429, 430, 454
See application file for complete search history.

(56) References Cited

U.S. PATENT DOCUMENTS

| 7,807,858 B2 | 10/2010 | Ishii et al. |
| 2006/0122146 A1 | 6/2006 | Chun et al. |
| 2008/0125589 A1 | 5/2008 | Ishii et al. |
| 2008/0139802 A1 | 6/2008 | Axt et al. |
| 2010/0056770 A1 | 3/2010 | Axt et al. |
| 2010/0267940 A1 | 10/2010 | Ishii et al. |
| 2011/0201825 A1 | 8/2011 | Ishii et al. |

FOREIGN PATENT DOCUMENTS

| JP | 2006-290870 A | 10/2006 |
| WO | WO 2006/031725 A2 | 3/2006 |
| WO | WO 2008/045419 A1 | 4/2008 |
| WO | WO 2009/025169 A1 | 2/2009 |
| WO | WO 2009/075186 A1 | 6/2009 |
| WO | WO 2010/047266 A1 | 4/2010 |

OTHER PUBLICATIONS

Corresponding International Search Report with English Translation dated May 31, 2011 (six (6) pages).
Theodora W. Greene et al., "Protective Group in Organic Synthesis", Reactivities, Reagents, and Reactivity Charts, 3$^{rd}$ edition, 1999, (twenty-six (26) pages).
Peiyuan Wang et al., "An Efficient and Diastereoselective Synthisis of PSI-6130: A Clinically Efficacious Inhibitor of HCV NS5B Polymerase", J. Org. Chem., 2009, vol. 74, No. 17, pp. 6819-6824.
Alexandre L'Heureux et al., "Aminodifluorosulfinium Salts: Selective Fluorination Reagents with Enhanced Thermal Stability and Ease of Handling", J. Org. Chem., 2010, vol. 75, No. 10, pp. 3401-3411.

*Primary Examiner* — Golam M M Shameem
(74) *Attorney, Agent, or Firm* — Crowell & Moring LLP

(57) ABSTRACT

In the presence invention, a (2R)-2-fluoro-2-C-methyl-D-ribono-γ-lactone precursor is produced in the form of a ring-opened fluorinated compound by reaction of a 1,2-diol with sulfuryl fluoride ($SO_2F_2$) in the presence of an organic base and, optionally, a fluoride ion source. The production method of the present invention secures less number of process steps as compared to the conventional production method (shortening of three steps: cyclic sulfurous esterification, oxidation and ring-opening fluorination to one step) and satisfies the requirements for industrial production (high yield and high reproductivity). The thus-obtained (2R)-2-fluoro-2-C-methyl-D-ribono-γ-lactone precursor is useful as an important intermediate for the synthesis of 2'-deoxy-2'-fluoro-2'-C-methylcytidine with antivirus activity.

4 Claims, No Drawings

METHOD FOR PRODUCING (2R)-2-FLUORO-2-C-METHYL-D-RIBONO-γ-LACTONE PRECURSOR

TECHNICAL FIELD

The present invention relates to a method for producing a (2R)-2-fluoro-2-C-methyl-D-ribono-γ-lactone precursor.

BACKGROUND ART

There have been reported some methods for production of (2R)-2-fluoro-2-C-methyl-D-ribono-γ-lactone precursors. In any of these production methods, the stereoselective introduction of a fluorine atom to 2-position is a significant problem. Ring-opening fluorination of a cyclic sulfuric ester is known as a fluorine atom introduction technique suitable for mass-scale production (see Patent Documents 1 and 2 and Non-Patent Document 1). Using this technique, it is feasible to produce a (2R)-2-fluoro-2-C-methyl-D-ribono-γ-lactone precursor in the form of a ring-opened fluorinated compound in three steps (first step: cyclic sulfurous esterification, second step: oxidation, third step: ring-opening fluorination) from a 1,2-diol substrate (see Scheme 1 where Me is a methyl group; Et is an ethyl group; $X^+$ is a proton, a protonated organic base, a metal cation, a tetraalkylammonium or a tris(dialkylamino)sulfonium; and Bz is a benzoyl group). There is also reported a modified production method for producing a ring-opened fluorinated compound in two steps (first step: cyclic sulfuric esterification, second step: ring-opening fluorination) from a 1,2-diol substrate by directly converting the 1,2-diol to a cyclic sulfuric ester with the use of sulfuryl chloride or 1,1'-sulfonyl diimidazole. However, the aforementioned three-step production method is suitably adopted rather than the modified two-step production method in order to obtain the ring-opened fluorinated compound with high yield and high reproductivity.

Scheme 1

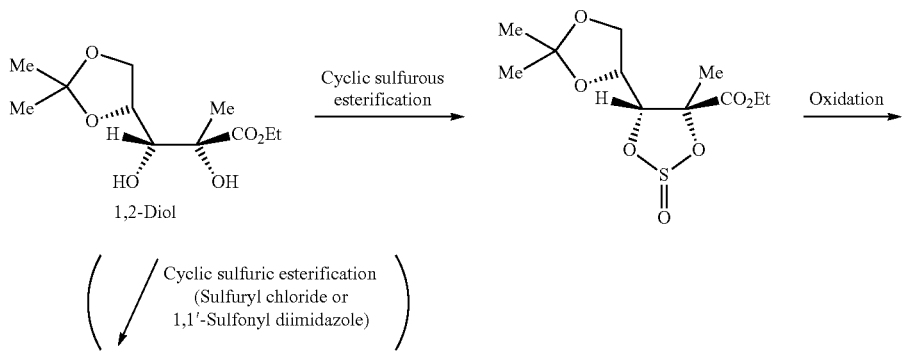

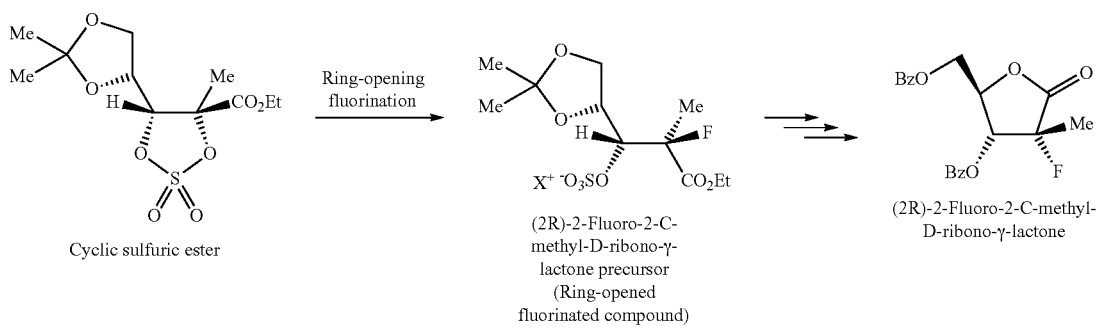

On the other hand, the present applicant has disclosed dehydroxyfluorination of an alcohol in the presence of sulfuryl fluoride ($SO_2F_2$) and an organic base (and optionally, a "salt or complex of an organic base and hydrogen fluoride") (see Patent Document 3).

PRIOR ART DOCUMENTS

Patent Documents

Patent Document 1: International Publication No. 2008/045419
Patent Document 2: International Publication No. 2006/031725
Patent Document 3: Japanese Laid-Open Patent Publication No. 2006-290870

Non-Patent Documents

Non-Patent Document 1: J. Org. Chem. (US), 2009, Vol. 74, P. 6819-6824

SUMMARY OF THE INVENTION

Problems to be Solved by the Invention

It is an object of the present invention to provide an industrial production method of a (2R)-2-fluoro-2-C-methyl-D-ribono-γ-lactone precursor.

The conventional production method in which the ring-opening fluorination of the cyclic sulfuric ester is involved has difficulty in achieving the requirements for industrial production (high yield and high reproducitvity) as well as the reduction of process steps. It is expected that, from the industrial viewpoint, the reduction of process steps leads to simplification of operation and reduction of waste so as to attain high productivity and low cost. There has thus been a strong demand to develop an industrial production method capable of producing a (2R)-2-fluoro-2-C-methyl-D-ribono-γ-lactone precursor, which is the target compound of the present invention, in less number of process steps than the conventional production method.

Further, it has not been reported that: sulfuryl fluoride functions as a cyclic sulfuric esterification agent for 1,2-diol, that is, the raw substrate material of the present invention. There has not been any report of domino reaction including cyclic esterification of 1,2-diol with the use of sulfuryl fluoride, followed by ring-opening fluorination of the esterification product.

Means for Solving the Problems

The present inventors have made extensive researches in view of the above problems and resultantly found that it is possible to produce a (2R)-2-fluoro-2-C-methyl-D-ribono-γ-lactone precursor in the form of a ring-opened fluorinated compound by reacting a 1,2-diol with sulfuryl fluoride in the presence of an organic base.

It is preferable that the ester moiety of the 1,2-diol as the raw substrate material, is either methyl ester or ethyl ester. It is also preferable that two hydroxyl groups at 4- and 5-positions in the 1,2-diol are protected by the same isopropylidene group. This substrate material is easily available on a mass scale. Further, it is preferable that the reaction is performed in the additional presence of a fluoride ion source selected from the group consisting of hydrogen fluoride, a "salt or complex of an organic base and hydrogen fluoride", a metal fluoride, a tetraalkylammonium fluoride, a "complex of a tetraalkylammonium fluoride and hydrogen fluoride" and a tris(dialkylamino)sulfonium trialkylsilyl difluoride in order to obtain the ring-opened fluorinated compound with high yield and high reproductivity.

The thus-obtained ring-opened fluorinated compound can be converted with high yield to a desired (2R)-2-fluoro-2-C-methyl-D-ribono-γ-lactone in a similar manner with reference to Patent Document 1, Patent Document 2, Non-Patent Document 1 or the like.

As mentioned above, the present inventors have found the particularly useful techniques for production of the (2R)-2-fluoro-2-C-methyl-D-ribono-γ-lactone precursor. The present invention is based on these findings.

Namely, the present invention provides a method for producing a (2R)-2-fluoro-2-C-methyl-D-ribono-γ-lactone precursor as set forth in [Inventive Aspect 1] to [Inventive Aspect 4].

[Inventive Aspect 1]
A method for producing a ring-opened fluorinated compound of the general formula [2], comprising: reacting a 1,2-diol of the general formula [1] with sulfuryl fluoride ($SO_2F_2$) in the presence of an organic base,

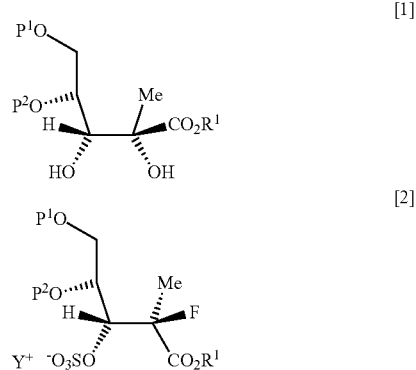

where Me represents a methyl group; $R^1$ represents an alkyl group or a substituted alkyl group; $P^1$ and $P^2$ each independently represent a hydroxyl protecting group; and $Y^+$ represents a proton or a protonated organic base.

[Inventive Aspect 2]
A method for producing a ring-opened fluorinated compound of the general formula [3], comprising: reacting a 1,2-diol of the general formula [1] with sulfuryl fluoride ($SO_2F_2$) in the presence of an organic base and a fluoride ion source selected from the group consisting of hydrogen fluoride, a salt or complex of an organic base and hydrogen fluoride, a metal fluoride, a tetraalkylammonium fluoride, a complex of a tetraalkylammonium fluoride and hydrogen fluoride and a tris(dialkylamino)sulfonium trialkylsilyl difluoride,

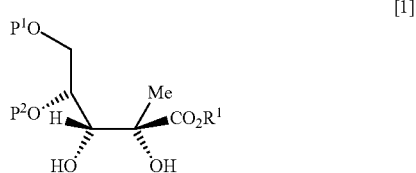

-continued

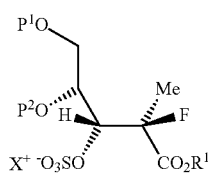

[3]

where Me represents a methyl group; $R^1$ represents an alkyl group or a substituted alkyl group; $P^1$ and $P^2$ each independently represent a hydroxyl protecting group; and $X^+$ represents a proton, a protonated organic base, a metal cation, a tetraalkylammonium or a tris(dialkylamino)sulfonium.

[Inventive Aspect 3]

A method for producing a ring-opened fluorinated compound of the general formula [5], comprising, reacting a 1,2-diol of the general formula [4] with sulfuryl fluoride ($SO_2F_2$) in the presence of an organic base,

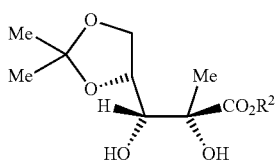

[4]

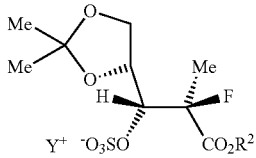

[5]

where Me represents a methyl group; $R^2$ represents a methyl group or an ethyl group; and $Y^+$ represents a proton or a protonated organic base.

[Inventive Aspect 4]

A method for producing a ring-opened fluorinated compound of the general formula [6], comprising: reacting a 1,2-diol of the general formula [4] with sulfuryl fluoride ($SO_2F_2$) in the presence of an organic base and a fluoride ion source selected from the group consisting of hydrogen fluoride, a salt or complex of an organic base and hydrogen fluoride, a metal fluoride, a tetraalkylammonium fluoride, a complex of a tetraalkylammonium fluoride and hydrogen fluoride and a tris(dialkylamino)sulfonium trialkylsilyl difluoride,

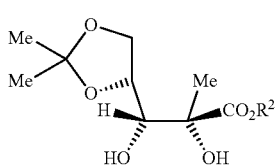

[4]

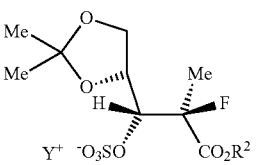

[6]

where Me represents a methyl group; $R^2$ represents a methyl group or an ethyl group; and $X^+$ represents a proton, a protonated organic base, a metal cation, a tetraalkylammonium or a tris(dialkylamino)sulfonium.

The present invention has the following advantages over the prior art.

In the present invention, the sulfuryl fluoride functions as a cyclic sulfuric esterification agent for the 1,2-diol and allows cyclic sulfuric esterification and subsequent ring-opening fluorination to proceed continuously in a domino reaction process by the action of a fluoride ion generated as a by-product of the cyclic sulfuric esterification (in the form of a salt with the organic base) (the reaction process proceeds more smoothly in the additional presence of the fluoride ion source) (see Scheme 2). The (2R)-2-fluoro-2-C-methyl-D-ribono-γ-lactone precursor can be thus produced as the ring-opened fluorinated compound in one step from the 1,2-diol substrate. Further, the ring-opened fluorinated compound can be obtained with high yield and high reproductivity by adoption of the suitable reaction substrate and reaction conditions.

Scheme 2

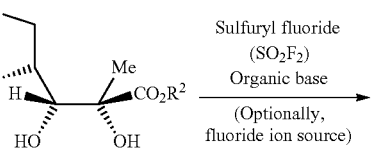

Suitable 1,2-diol

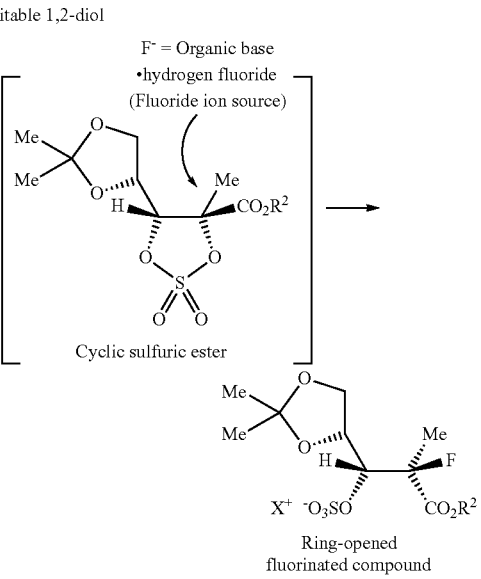

The present invention is advantageous over Patent Documents 1 and 2 and Non-Patent Document 1 in that it is possible in the present invention to ensure the less number of process steps as compared to the conventional production method and, at the same time, satisfy the requirements for industrial application.

It has been shown that, even when a 1,2-diol having a 3-position hydroxyl group protected by a benzoyl group (3-position protected alcohol) was reacted with sulfuryl fluoride in the presence of an organic base and a fluoride ion source, the resulting 3-position protected fluorinated compound was obtained with very low yield (see Scheme 3 and Comparative Example 1; for information, the desired dehydroxyfluorination of the 3-position protected alcohol proceeds favorably with the use of diethylaminosulfur trifluoride (DAST) or (2-methoxyethyl)amonosulfur trichloride (Deoxofluor) as disclosed in International Publication No. 2006/012440).

This result leads to a conclusion that it is essential that the cyclic sulfuric ester is derived as a reaction intermediate from the 1,2-diol in the present reaction process for efficient introduction of a fluorine atom to 2-position and goes beyond the disclosure of Patent Document 3.

Scheme 3

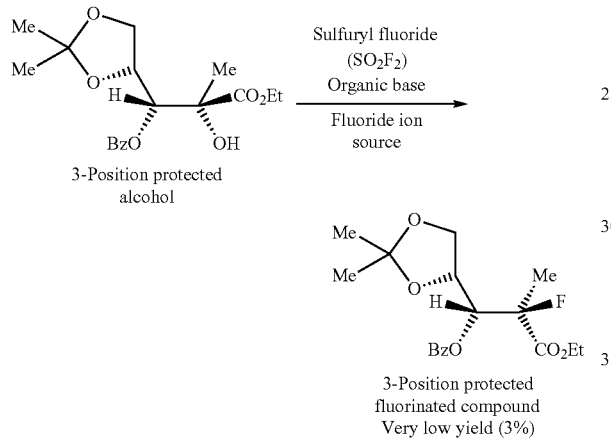

3-Position protected fluorinated compound
Very low yield (3%)

DETAILED DESCRIPTION OF THE EMBODIMENTS

Hereinafter, the production method of the (2R)-2-fluoro-2-C-methyl-D-ribono-γ-lactone precursor according to the present invention will be described in detail below.

In the present invention, a ring-opened fluorinated compound of the general formula [2] is produced by reaction of a 1,2-diol of the general formula [1] with sulfuryl fluoride in the presence of an organic base and, optionally, a fluoride ion source. The steric configuration of 2-position carbon (i.e. carbon subjected to dehydroxyfluorination) is inverted during the reaction, whereas the steric configuration of 3-position carbon (i.e. carbon formed into a sulfuric ester) and the steric configuration of the 4-position carbon (i.e. carbon to which a secondary hydroxyl protecting group is bonded) are maintained throughout the reaction.

In the 1,2-diol of the general formula [1], Me represents a methyl group.

Further, $R^1$ represents an alkyl group or a substituted alkyl group in the 1,2-diol of the general formula [1]. Examples of the alkyl group are those having 1 to 12 carbon atoms in the form of a linear structure, a branched structure or a cyclic structure (in the case of 3 or more carbon atoms). Examples of the substituted alkyl group are those obtained by substitution of any number of and any combination of substituents onto any of carbon atoms of the above alkyl group. As such substituents, there can be used: halogen atoms such as fluorine, chlorine, bromine and iodine; lower alkyl groups such as methyl, ethyl, propyl and butyl; and lower alkoxy groups such as methoxy, ethoxy, propoxy and butoxy. In the present specification, the term "lower" means that the group to which the term is attached has 1 to 6 carbon atoms in the form of a linear structure, a branched structure or a cyclic structure (in the case of 3 or more carbon atoms). Among others, alkyl or substituted alkyl groups of 1 to 4 carbon atoms are preferred. Particularly preferred are methyl and ethyl (as $R^2$).

In the 1,2-diol of the general formula [1], $P^1$ and $P^2$ represent protecting groups for respective hydroxyl groups. Examples of the protecting group are those described in "Protective Groups in Organic Synthesis", Third Edition, 1999, John Wiley & Sons, Inc. Herein, $P^1$ and $P^2$ can be of the same kind or of different kinds. Alternatively, one protection group may be adopted as $P^1$ and $P^2$. It is preferable to adopt one protecting group, more preferably isopropylidene group, as $P^1$ and $P^2$ (see FIG. 1).

FIG.1

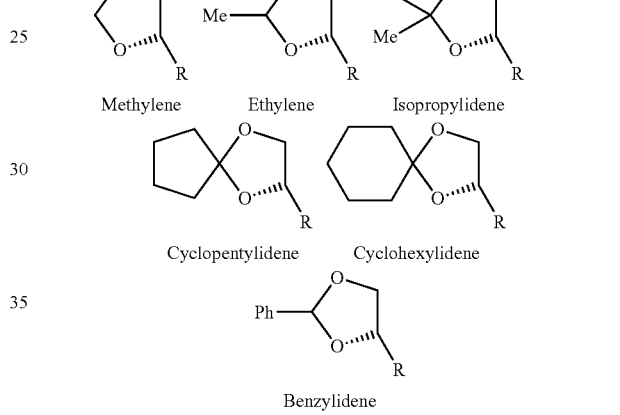

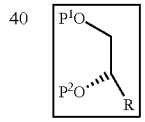

R: Residue of general formula [1]
Ph: Phenyl

The 1,2-diol of the general formula [1] can be prepared in a similar manner with reference to Patent Document 1, Patent Document 2, Non-Patent Document 1 or the like.

It suffices to use the sulfuryl fluoride in an amount of 0.7 mol or more per 1 mol of the 1,2-diol of the general formula [1]. The amount of the sulfuryl fluoride used is preferably 0.8 to 20 mol, more preferably 0.9 to 15 mol, per 1 mol of the 1,2-diol of the general formula [1].

Examples of the organic base are trimethylamine, triethylamine, diisopropylethylamine, tri-n-propylamine, tri-n-butylamine, N-methylpiperidine, pyridine, 2,6-lutidine, 2,4,6-collidine, 4-dimethylaminopyridine (DMAP), 1,5-diazabicyclo[4.3.0]non-5-ene (DBN) and 1,8-diazabicyclo[5.4.0]undec-7-ene (DBU). The organic base is not however limited to the above examples. It is feasible to apply any organic base commonly used for organic synthesis. Among others, triethylamine, diisopropylethylamine, tri-n-propylamine, tri-n-butylamine, pyridine, 2,6-lutidine, 4-dimethylaminopyridine, 1,5-diazabicyclo[4.3.0]non-5-ene and 1,8-diazabicyclo[5.4.0]undec-7-ene are preferred. Particularly preferred are triethylamine, diisopropylethylamine, 2,6-lutidine, 4-dimethylaminopyridine 1,5-diazabicyclo[4.3.0]non-5-ene and 1,8-diazabicyclo[5.4.0]undec-7-ene. In the case of using strongly basic 1,5-diazabicyclo[4.3.0]non-5-ene or 1,8-diazabicyclo[5.4.0]undec-7-ene as the organic base, the ring-opened fluorinated compound can be obtained with high yield and high reproductivity. Thus, the use of such strongly basic 1,5-diazabicyclo[4.3.0]non-5-ene or 1,8-diazabicyclo[5.4.0]undec-7-ene is one preferred embodiment of the present invention. The above organic bases can be used solely or in combination of two or more thereof.

It suffices to use the organic base in an amount of 0.7 mol or more per 1 mol of the 1,2-diol of the general formula [1]. The amount of the organic base used is preferably 0.8 to 20 mol, more preferably 0.9 to 15 mol, per 1 mol of the 1,2-diol of the general formula [1].

Examples of the fluoride ion source are hydrogen fluoride, a "salt or complex of an organic base and hydrogen fluoride", a metal fluoride, a tetraalkylammonium fluoride, a "complex of a tetraalkylammonium fluoride and hydrogen fluoride" and a tris(dialkylamino)sulfonium trialkylsilyl difluoride. These fluoride ion sources can be used solely or in combination of two or more thereof.

As the organic base in the "salt or complex of the organic base and hydrogen fluoride", there can be used trimethylamine, triethylamine, diisopropylethylamine, tri-n-propylamine, tri-n-butylamine, N-methylpiperidine, pyridine, 2,6-lutidine, 2,4,6-collidine, 4-dimethylaminopyridine, 1,5-diazabicyclo[4.3.0]non-5-ene, 1,8-diazabicyclo[5.4.0]undec-7-ene or the like. The organic base is not however limited to these examples. It is feasible to apply any organic base commonly used for organic synthesis. Among others, triethylamine, diisopropylethylamine, tri-n-propylamine, tri-n-butylamine, pyridine, 2,6-lutidine, 4-dimethylaminopyridine, 1,5-diazabicyclo[4.3.0]non-5-ene and 1,8-diazabicyclo[5.4.0]undec-7-ene are preferred. Particularly preferred are triethylamine, diisopropylethylamine, 2,6-lutidine, 4-dimethylaminopyridine 1,5-diazabicyclo[4.3.0]non-5-ene and 1,8-diazabicyclo[5.4.0]undec-7-ene. In the case of using strongly basic 1,5-diazabicyclo[4.3.0]non-5-ene or 1,8-diazabicyclo[5.4.0]undec-7-ene as the organic base in the salt or complex of the organic base and hydrogen fluoride, the ring-opened fluorinated compound can be obtained with high yield and high reproductivity. Thus, the use of such strongly basic 1,5-diazabicyclo[4.3.0]non-5-ene or 1,8-diazabicyclo[5.4.0]undec-7-ene is one preferred embodiment of the present invention. The above organic bases can be used solely or in combination of two or more thereof in the "salt or complex of the organic base and hydrogen fluoride".

It suffices that the mol ratio of the organic base and hydrogen fluoride in the "salt or complex of the organic base and hydrogen fluoride" is in the range of 100:1 to 1:100. The mol ratio of the organic base and hydrogen fluoride is preferably 50:1 to 1:50, more preferably 25:1 to 1:25. It is convenient to use a complex of 1 mol triethylamine and 3 mol hydrogen fluoride or a complex of up to 30% (up to 10 mol %) pyridine and up to 70% (90 mol %) hydrogen fluoride, both of which are commercially available from Aldrich Chemical Co. (Aldrich Catalog 2009-2010).

As the metal fluoride, there can be used potassium fluoride, rubidium fluoride, silver fluoride or cesium fluoride. Among others, potassium fluoride, silver fluoride and cesium fluoride are preferred. Particularly preferred are potassium fluoride and cesium fluoride.

As the tetraalkylammonium fluoride, there can be used those represented by the general formula [7]

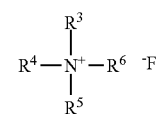

[7]

where $R^3$, $R^4$, $R^5$ and $R^6$ each independently represent an alkyl group. Examples of the alkyl groups $R^3$, $R^4$, $R^5$ and $R^6$ are those having 1 to 12 carbon atoms in the form of a linear structure, a branched structure or a cyclic structure (in the case of 3 or more carbon atoms). Among others, alkyl groups of 1 to 6 carbon atoms are preferred. It is particularly preferable that all of these four alkyl groups are the same alkyl group of 1 to 6 carbon atoms.

The same results can be obtained even when the tetraalkylammonium fluoride is in hydrate form. Thus, the claimed tetraalkylammonium fluoride includes a hydrate thereof. There is no particular limitation on the hydration number of the tetraalkylammonium fluoride hydrate. It is convenient to use tetraethylammonium fluoride dihydrate [$(C_2H_5)_4$NF$\cdot$2H$_2$O] or tetra-n-butylammmonium fluoride trihydrate [$(C_4H_9)_4$NF$\cdot$3H$_2$O], both of which are commercially available from Aldrich Chemical Co. (Aldrich Catalog 2009-2010).

In the "complex of the tetraalkylammonium fluoride and hydrogen fluoride", there can be used the same tetraalkylammonium fluoride as above. (Preferred forms of the tetraalkylammonium fluoride are also the same as above.)

It suffices that the mol ratio of the tetraalkylammonium fluoride and hydrogen fluoride in the "complex of the tetraalkylammonium fluoride and hydrogen fluoride" is in the range of 100:1 to 1:100. The mol ratio of the tetraalkylammonium fluoride and hydrogen fluoride is preferably 50:1 to 1:50, more preferably 25:1 to 1:25. It is convenient to use tetraethylammonium fluoride trihydrofluoride or tetra-n-butylammonium fluoride dihydrofluoride, both of which are commercially available from Tokyo Chemical Industry Co., Ltd. (TCI Catalog 2010).

As the tris(dialkylamino)sulfonium trialkylsilyl difluoride, there can be used those represented by the general formula [8]

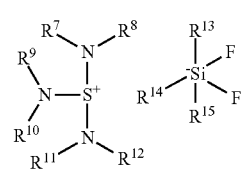

[8]

where $R^7$, $R^8$, $R^9$, $R^{10}$, $R^{11}$, $R^{12}$, $R^{13}$, $R^{14}$ and $R^{15}$ each independently represent an alkyl group.

Examples of the alkyl groups $R^7$, $R^8$, $R^9$, $R^{10}$, $R^{11}$, $R^{12}$, $R^{13}$, $R^{14}$ and $R^{15}$ are those having 1 to 12 carbon atoms in the form of a linear structure, a branched structure or a cyclic structure (in the case of 3 or more carbon atoms). Among others, alkyl groups of 1 to 6 carbon atoms are preferred. It is particularly preferable that all of the six alkyl groups $R^7$, $R^8$, $R^9$, $R^{10}$, $R^{11}$ and $R^{12}$ are the same alkyl group of 1 to 6 carbon atoms and, at the same time, all of three alkyl groups $R^{13}$, $R^{14}$ and $R^{15}$ are the same alkyl group of 1 to 6 carbon atoms.

It suffices to use the fluoride ion source in an amount of 0.1 mol or more per 1 mol of the 1,2-diol of the general formula [1]. The amount of the fluoride ion source used is preferably 0.3 to 50 mol, more preferably 0.5 to 25 mol, per 1 mol of the 1,2-diol of the general formula [1].

The present reaction proceeds smoothly under basic conditions. It is thus preferable to, in the case where the reaction system becomes acidic, increase the amount of the organic base used as the reaction agent (distinguished from the organic base in the "salt or complex of the organic base and hydrogen fluoride") and thereby control the reaction system to be basic.

Further, the present reaction can be performed in a reaction solvent. Example of the reaction solvent are: aliphatic hydrocarbon solvents such as n-hexane and n-heptane; aromatic hydrocarbon solvents such as toluene and xylene; halogenated solvents such as methylene chloride and 1,2-dichloroethane; ether solvents such as tetrahydrofuran and tert-butyl methyl ether; ester solvents such as ethyl acetate and n-butyl acetate; amide solvents such as N,N-dimethylformamide and 1,3-dimethyl-2-imidazolidinone; nitrile solvents such as acetonitrile and propionitrile; and dimethyl sulfoxide. Among others, n-heptane, toluene, methylene chloride, tetrahydrofuran, ethyl acetate, N,N-dimethylformamide, acetonitrile and dimethyl sulfoxide are preferred. Particularly preferred are toluene, tetrahydrofuran, ethyl acetate, n,n-dimethylformamide and acetonitrile. The above reaction solvents can be used solely or in combination of two or more thereof.

It suffice to use the reaction solvent in an amount of 0.1 L or more per 1 mol of the 1,2-diol of the general formula [1]. The amount of the reaction solvent used is preferably 0.2 to 30 L, more preferably 0.3 to 20 L, per 1 mol of the 1,2-diol of the general formula [1]. Alternatively, the present reaction can be performed in the presence of no solvent (i.e. under neat conditions).

It suffices that the reaction temperature is in the range of −30 to +200° C. The reaction temperature is preferably in the range of −20 to +175° C., more preferably −10 to +150° C.

It suffices that the reaction time is in the range of 48 hours or less. As the reaction time varies depending on the raw substrate material and the reaction conditions, it is preferable to determine the time at which the raw substrate material has almost disappeared as the end of the reaction while monitoring the progress of the reaction by any analytical means such as gas chromatography, liquid chromatography or nuclear magnetic resonance.

In some cases, the present reaction may proceed smoothly in the presence of an additive such as a phase transfer catalyst e.g. quaternary ammonium salt, quaternary phosphonium salt, crown ether, diglyme or polyethylene glycol or a synthetic zeolite e.g. molecular sieves. By adoption of the suitable substrate material and reaction conditions, the reaction is not however necessarily performed in the presence of such an additive.

The ring-opened fluorinated compound of the general formula [2] can be obtained by post-treatment. It is feasible to apply ordinary post-treatment operation for organic synthesis.

In the ring-opened fluorinated compound of the general formula [2], $R^1$, $P^1$ and $P^2$ are the same as those in the 1,2-diol of the general formula [1] and are not changed throughout the reaction.

In the ring-opened fluorinated compound of the general formula [2], $Y^+$ represents a proton or a protonated organic base. The protonated organic base is the one derived from the organic base used as the reaction agent.

The ring-opened fluorinated compound can preferably be obtained in the form of the general formula [3] or [6] by adoption of the suitable substrate material or by adoption of the suitable substrate material and reaction conditions. In the ring-opened fluorinated compound of the general formula [3] or [6], $X^+$ represents a proton, a protonated organic base, a metal cation, a tetraalkylammonium or a tris(dialkylamino)sulfonium. In this case, the protonated organic base is one derived from the organic base used as the reaction agent or from the organic base in the "salt or complex of the organic base and hydrogen fluoride" used as the fluoride ion source. The metal cation, the tetraalkylammonium and the tris(dialkylamino)sulfonium are those derived from the metal fluoride, the tetraalkylammonium fluoride or "complex of the tetraalkylammonium fluoride and hydrogen fluoride" and the tris(dialkylamino)sulfonium trialkylsilyl difluoride, respectively.

Depending on the raw substrate material, reaction conditions and post-treatment conditions, a sulfuric ester moiety (—OSO$_3^-$X$^+$) of the ring-opened fluorinated compound may be hydrolyzed to form a hydrolysate product (—OH). As the hydrolysate product is secondarily generated after the production of the ring-opened fluorinated compound, it is regarded that the reaction even in which the hydrolysate product is obtained as a main product is also in the scope of the present invention.

As the ordinary post-treatment operation, it is feasible to obtain the ring-opened fluorinated compound as a crude product by adding water or an aqueous solution of an inorganic acid or base to the reaction-terminated liquid, extracting the resulting liquid with an organic solvent and concentrating the recovered organic layer. The crude product can be purified to a high purity level as needed by activated carbon treatment, recrystallization, column chromatography or the like.

The thus-obtained ring-opened fluorinated compound can be converted to a (2R)-2-fluoro-2-C-methyl-D-ribono-γ-lactone in a similar manner with reference to Patent Document 1, Patent Document 2, Non-Patent Document 1 or the like (see Scheme 4). It is feasible to directly subject the reaction-terminated liquid to hydrolysis, or hydrolysis, deprotection and lactonization in series as one-pot reaction, by omitting the post treatment operation for separation of the ring-opened fluorinated compound (and purging the remaining sulfuryl fluoride out of the reaction system as needed). In this case, total yield improvement may be expected as compared to the case of performing the conversion reaction to produce the (2R)-2-fluoro-2-C-methyl-D-ribono-γ-lactone after once separating the ring-opened fluorinated compound from the reaction-terminated liquid.

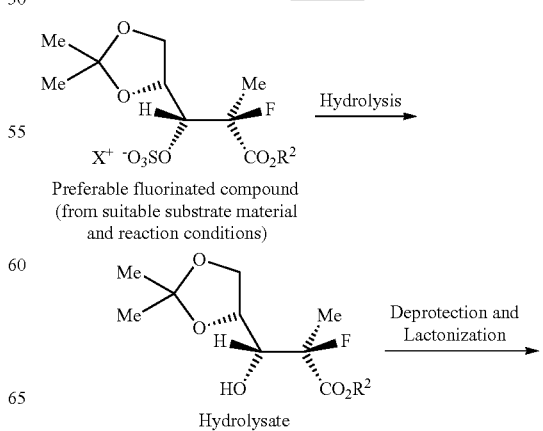

Scheme 4

-continued

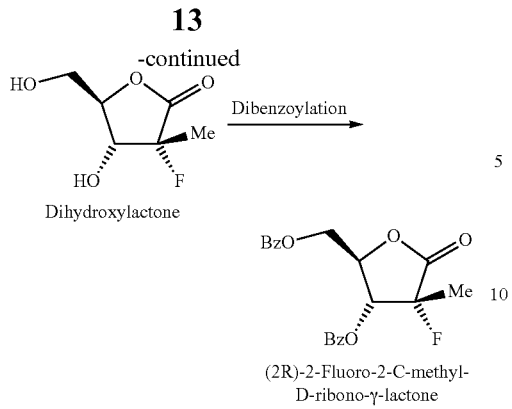

Dihydroxylactone (2R)-2-Fluoro-2-C-methyl-
D-ribono-γ-lactone

EXAMPLES

The present invention will be described in more detail below by way of the following examples. It should be noted that the following examples are illustrative and are not intended to limit the present invention thereto. Herein, Examples 1 to 7, 9 and 10 are each directed to synthesis of a (2R)-2-fluoro-2-C-methyl-D-ribono-γ-lactone precursor in the presence of a fluoride ion source; and Comparative Example 1 and Example 8 are each directed to synthesis of a (2R)-2-fluoro-2-C-methyl-D-ribono-γ-lactone precursor in the absence of a fluoride ion source. The detailed procedures of the respective synthesis reactions are as mentioned below. In the following examples, i-Pr represents isopropyl.

Example 1

A pressure-proof reaction vessel of stainless steel (SUS) was charged with 249 mg (1.00 mmol, 1.00 eq) of 1,2-diol of the following formula, 5 mL (5 L/mol) of acetonitrile, 670 mg (6.62 mmol, 6.62 eq) of triethylamine ($Et_3N$) and 407 mg (1.94 mmol, 1.94 eq) of tetraethylammonium fluoride trihydrofluoride ($Et_4NF \cdot 3HF$), followed by blowing 816 mg (8.00 mmol, 8.00 eq) of sulfuryl fluoride ($SO_2F_2$) at −15° C. from a cylinder into the reaction vessel.

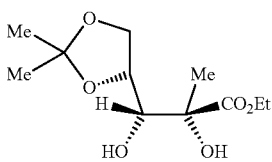

The resulting liquid was stirred for 5 hours at 90° C. (The same reaction was performed separately. It was confirmed by gas chromatography analysis of the reaction product that a cyclic sulfuric ester was generated in the initial stage of the reaction. (The standard of the cyclic sulfuric ester was synthesized with reference to Non-Patent Document 1.)). To the thus-obtained reaction-terminated liquid, an aqueous potassium carbonate solution (prepared from 1.40 g (10.1 mmol, 10.1 eq) of potassium carbonate and 20 mL of water) was added. After that, the reaction-terminated solution was extracted with 30 mL of ethyl acetate. The recovered aqueous layer was again extracted with 30 mL of ethyl acetate. The recovered organic layers were combined. The combined organic layer was dried with anhydrous sodium sulfate, concentrated under reduced pressure and dried under vacuum.

With this, a crude product of ring-opened fluorinated compound of the following formula was obtained (where $Z^+$ was proton, protonated triethylamine, tetraethylammonium or potassium (derived from the aqueous potassium carbonate solution added for post-treatment operation)).

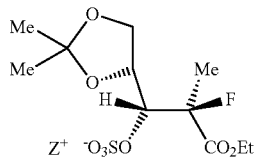

It was confirmed by $^{19}F$-NMR quantification analysis (internal standard method) of the crude product that the target compound of the above formula was contained in an amount of 660 The yield was 66%.

The $^{19}F$-NMR analysis results of the crude product are indicated below. $^{19}F$-NMR [standard material: $C_6F_6$, deuterated solvent: $CDCl_3$] δ ppm: −8.23 (m, 1F).

The whole of the above-obtained crude product (660 μmol) was mixed with 2 mL (3 L/mol) of tetrahydrofuran, 1.69 g (16.2 mmol, 24.5 eq) of 2,2-dimethoxypropane and 500 μL (6.00 mmol, 9.09 eq) of 12 N hydrochloric acid. The resulting liquid was stirred for 3 hours at room temperature. To the-obtained reaction-terminated liquid, 6 mL of saturated aqueous sodium hydrogencarbonate solution was added. After that, the reaction-terminated liquid was extracted with 20 mL of ethyl acetate. The recovered aqueous layer was again extracted with 20 mL of ethyl acetate. The recovered organic layers were combined. The combined organic layer was dried with anhydrous sodium sulfate, concentrated under reduced pressure and dried under vacuum. With this, a crude product of hydrolysate of the following formula was obtained.

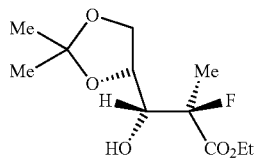

The $^{19}F$-NMR analysis results of the crude product are indicated below. $^{19}F$-NMR [standard material: $C_6F_6$, deuterated solvent: $CDCl_3$] δ ppm: −9.00 (m, 1F).

The whole of the above-obtained crude (regarded as 660 μmol) was mixed with 4 mL (6 L/mol) of ethanol and 100 μL (1.20 mmol, 1.82 eq) of 12 N hydrochloric acid. The resulting mixture was stirred for 21 hours at room temperature. The thus-obtained reaction-terminated liquid was concentrated under reduced pressure, subjected twice to azeotropic concentration with 20 mL of toluene under reduced pressure and dried under vacuum. With this, a crude product of dihydroxylactone of the following formula was obtained.

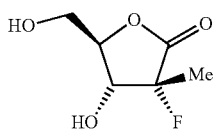

The $^{19}F$-NMR analysis results of the crude product are indicated below.

$^{19}F$-NMR [standard material: $C_6F_6$, deuterated solvent: $CDCl_3$] δ ppm: −9.64 (m, 1F).

The whole of the above-obtained crude product (regarded as 660 μmol) was mixed with 2.45 g (31.0 mmol, 47.0 eq) of pyridine, followed by adding thereto 750 mg (5.34 mmol, 8.09 eq) of benzoyl chloride under ice cooling. The resulting liquid was stirred for 30 minutes at room temperature. To the thus-obtained reaction-terminated liquid, 2 mL of water was added under ice cooling. The reaction-terminated liquid was further stirred for 10 minutes at room temperature and concentrated under reduced pressure. The concentration residue was admixed with 10 mL of saturated aqueous sodium hydrogencarbonate solution and extracted with 20 mL of ethyl acetate. The recovered aqueous layer was again extracted with 20 mL of ethyl acetate. The recovered organic layers were combined. The combined organic layer was dried with anhydrous sodium sulfate, concentrated under reduced pressure and dried under vacuum. There was thus obtained a crude product of (2R)-2-fluoro-2-C-methyl-D-ribono-γ-lactone of the following formula.

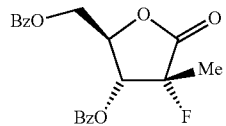

It was confirmed by $^{19}$F-NMR quantification analysis (internal standard method) of the crude product that the target compound of the above formula was contained in an amount of 380 μmol. The total yield from the 1,2-diol substrate was 38%.

The $^{19}$F-NMR analysis results of the crude product are indicated below. $^{19}$F-NMR [standard material: $C_6F_6$, deuterated solvent: $CDCl_3$] δ ppm: −5.44 (m, 1F).

Examples 2 to 7

The reaction was performed in the same manner as in Example 1, except for changing the organic base and the fluoride ion source.

The results of Examples 1 to 7 are summarized in TABLE 1.

TABLE 1

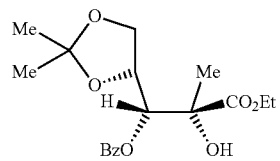

| | Organic base | Fluoride ion source | Ring-Opened fluorinated compound | (2R)-2-Fluoro-2-C-methyl-D-ribono-γ-lactone |
|---|---|---|---|---|
| Example 1 | Et$_3$N (6.62 eq) | Et$_4$NF•3HF (1.94 eq) | 66% | 38% |
| Example 2 | i-Pr$_2$NEt (10.0 eq) | i-Pr$_2$NEt•3HF (3.00 eq) | 30% | — |
| Example 3 | Et$_3$N (3.00 eq) | Et$_3$N•3HF (1.00 eq) | 41% | 26% |
| Example 4 | Et$_3$N (3.30 eq) | Et$_4$NF•3HF (1.00 eq) | 46% | 29% (21%) |
| Example 5 | Et$_3$N (9.00 eq) | Et$_3$N•3HF (2.00 eq) | 51% | — |
| Example 6 | DBU (6.00 eq) | Et$_3$N•3HF (2.00 eq) | 85% | 55% |
| Example 7 | DBU (9.00 eq) | Et$_3$N•3HF (2.00 eq) | 86% | 54% |

Comparative Example 1

A pressure-proof reaction vessel of stainless steel (SUS) was charged with 179 mg (508 μmol, 1.00 eq) of 3-position protected alcohol of the following formula, 2.5 mL (5 L/mol) of acetonitrile, 158 mg (1.56 mmol, 3.07 eq) of triethylamine and 92.0 mg (571 μmol, 1.12 eq) of triethylamine trihydrofluoride, followed by blowing 415 mg (4.07 mmol, 8.01 eq) of sulfuryl fluoride at −15° C. from a cylinder into the reaction vessel.

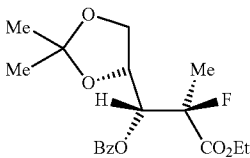

The resulting liquid was stirred for 5 hours at 90° C. To the thus-obtained reaction-terminated liquid, an aqueous potassium carbonate solution (prepared from 800 mg (5.79 mmol, 11.4 eq) of potassium carbonate and 10 mL of water) was added. After that, the reaction-terminated solution was extracted with 15 mL of ethyl acetate. The recovered aqueous layer was again extracted with 15 mL of ethyl acetate. The recovered organic layers were combined. The combined organic layer was dried with anhydrous sodium sulfate, concentrated under reduced pressure and dried under vacuum. With this, a crude product of 3-position protected fluorinated compound of the following formula was obtained.

It was confirmed by $^{19}$F-NMR quantification analysis (internal standard method) of the crude product that the target compound of the above formula was contained in an amount of 15.2 μmol. The yield was 3%. (A large amount of 3-position protected alcohol substrate was recovered.)

The $^{19}$F-NMR analysis results of the crude product are indicated below. $^{19}$F-NMR [standard material: $C_6F_6$, deuterated solvent: $CDCl_3$] δ ppm: −6.20 (m, 1F).

Example 8

A pressure-proof reaction vessel of stainless steel (SUS) was charged with 4.91 g (21.0 mmol, 1.00 eq) of 1,2-diol of the following formula, 22 mL (1 L/mol) of acetonitrile and 7.38 g (48.5 mmol, 2.31 eq) of 1,8-diazabicyclo[5.4.0]undec-7-ene (DBU), followed by blowing 6.10 g (59.8 mmol, 2.85 eq) of sulfuryl fluoride ($SO_2F_2$) at −15° C. from a cylinder into the reaction vessel.

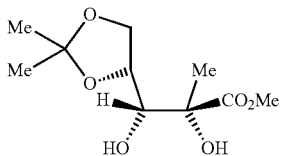

The resulting liquid was stirred for 2 hours and 30 minutes at 55° C. (The same reaction was performed separately. It was confirmed by gas chromatography analysis of the reaction product that a cyclic sulfuric ester was generated in the initial stage of the reaction. (The standard of the cyclic sulfuric ester was synthesized with reference to Non-Patent Document 1.)). To the thus-obtained reaction-terminated liquid, an aqueous potassium carbonate solution (prepared from 4.50 g (32.6 mmol, 1.55 eq) of potassium carbonate and 30 mL of water) was added. After that, the reaction-terminated solution was extracted with 60 mL of ethyl acetate. The recovered aqueous layer was again extracted with 60 mL of ethyl acetate. The recovered organic layers were combined. The combined organic layer was dried with anhydrous sodium sulfate, concentrated under reduced pressure and dried under vacuum. With this, a curde product of ring-opened fluorinated compound of the following formula was obtained (where $Z^+$ was proton, protonated 1,8-diazabicyclo[5.4.0]undec-7-ene or potassium (derived from the aqueous potassium carbonate solution added for post-treatment operation)).

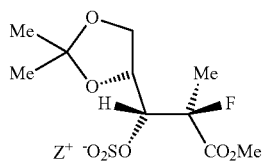

It was confirmed by $^{19}$F-NMR quantification analysis (internal standard method) of the crude product that the target compound of the above formula was contained in an amount of 18.5 mmol. The yield was 88%.

The $^{19}$F-NMR analysis results of the crude product are indicated below. $^{19}$F-NMR [standard material: $C_6F_6$, deuterated solvent: $CDCl_3$] δ ppm: −8.47 (m, 1F).

The whole of the above-obtained crude product (18.5 mmol) was mixed with 11 mL (0.6 L/mol) of 1,4-dioxane, 8.75 g (84.0 mmol, 4.54 eq) of 2,2-dimethoxypropane and 380 mg (21.1 mmol, 1.14 eq) of water. The pH of the resulting liquid was controlled to 2 to 3 with the addition of 98% concentrated sulfuric acid under ice cooling. Then, the liquid was stirred for 16 hours at room temperature. To the thus-obtained reaction-terminated liquid, 20 mL of saturated aqueous sodium hydrogencarbonate solution was added. After that, the reaction-terminated liquid was extracted with 40 mL of ethyl acetate. The recovered aqueous layer was again extracted with 30 mL of ethyl acetate. The recovered organic layers were combined. The combined organic layer was dried with anhydrous sodium sulfate, concentrated under reduced pressure and dried under vacuum. With this, a crude product of hydrolysate of the following formula was obtained.

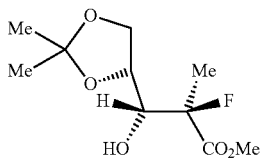

The $^{19}$F-NMR analysis results of the crude product are indicated below. $^{19}$F-NMR [standard material: $C_6F_6$, deuterated solvent: $CDCl_3$] δ ppm: −9.44 (m, 1F).

The whole of the above-obtained crude product (regarded as 18.5 mmol) was mixed with 21 mL (1 L/mol) of ethanol and 500 μL (6.00 mmol, 0.324 eq) of 12 N hydrochloric acid. The resulting liquid was stirred for 18 hours at room temperature. The thus-obtained reaction-terminated liquid was concentrated under reduced pressure, subjected twice to azeotropic concentration with 20 mL of toluene under reduced pressure and dried under vacuum. With this, a crude product of dihydroxylactone of the following formula was obtained.

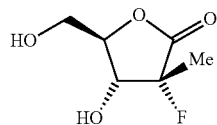

The $^{19}$F-NMR analysis results of the crude product were the same as those of Example 1.

The whole of the above-obtained crude product (regarded as 18.5 mmol) was mixed with 31 mL (2 L/mol) of acetonitrile and 4.90 g (61.9 mmol, 3.35 eq) of pyridine, followed by adding thereto 8.72 g (62.0 mmol, 3.35 eq) of benzoyl chloride under ice cooling. The resulting liquid was stirred for 7 hours at room temperature. To the thus-obtained reaction-terminated liquid, 20 mL of water was added under ice cooling. The reaction-terminated liquid was further stirred for 10 minutes at room temperature and extracted with 40 mL of ethyl acetate. The recovered organic layer was washed with 10 mL of 10% sodium chloride solution, dried with anhydrous sodium sulfate, concentrated under reduced pressure and dried under vacuum. There was thus obtained 10.9 g of a crude product of (2R)-2-fluoro-2-C-methyl-D-ribono-γ-lactone of the following formula.

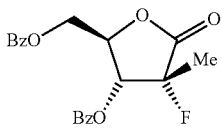

It was confirmed by $^{19}$F-NMR quantification analysis (internal standard method) of the crude product that the target compound of the above formula was contained in an amount of 15.6 mmol. The total yield from the 1,2-diol substrate was 74%. The $^{19}$F-NMR analysis results of the crude product were the same as those of Example 1.

The whole of, that is, 10.9 g (15.6 mmol) of the above-obtained crude product was recrystallized with a mixed solvent of 44 mL (4 vol) of ethyl acetate and 110 mL (10 vol) of n-heptane. With this, 4.87 g (13.1 mmol) of the (2R)-2-fluoro-2-C-methyl-D-ribono-γ-lactone of the above formula was obtained as a purified product (pale yellow-white crystalline substance). The recovery was 84%. The gas chromatographic purity of the purified product was 100%.

Example 9

A pressure-proof reaction vessel of stainless steel (SUS) was charged with 58.7 g (251 mmol, 1.00 eq) of 1,2-diol of the following formula, 250 mL (1 L/mol) of acetonitrile, 55.6 g (549 mmol, 2.19 eq) of triethylamine (Et₃N) and 64.4 g (374 mmol, 1.49 eq) of 1,8-diazabicyclo[5.4.0]undec-7-ene hydrofluoride (DBU·HF), followed by blowing 41.4 g (406 mmol, 1.62 eq) of sulfuryl fluoride (SO₂F₂) at 0° C. from a cylinder into the reaction vessel.

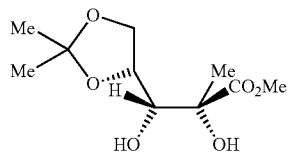

The resulting liquid was stirred for 5 hours at 55° C. To the thus-obtained reaction-terminated liquid, an aqueous potassium carbonate solution (prepared from 43.6 g (315 mmol, 1.25 eq) of potassium carbonate and 125 mL of water) was added. After that, the reaction-terminated solution was extracted with 250 mL of ethyl acetate. The recovered aqueous layer was again extracted with 125 mL of ethyl acetate. The recovered organic layers were combined. The combined organic layer was concentrated under reduced pressure and subjected three times to azeotropic concentration with 50 mL of toluene. With this, a curde product of ring-opened fluorinated compound of the following formula was obtained (where Z⁺ was proton, protonated triethylamine, protonated 1,8-diazabicyclo[5.4.0]undec-7-ene or potassium (derived from the aqueous potassium carbonate solution added for post-treatment operation)).

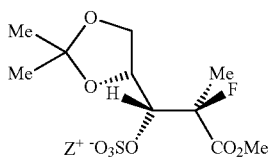

It was confirmed by ¹⁹F-NMR quantification analysis (internal standard method) of the crude product that the target compound of the above formula was contained quantitatively. The ¹⁹F-NMR analysis results of the crude product were the same as those of Example 8.

The whole of the above-obtained crude product (regarded as 251 mmol) was mixed with 125 mL (0.5 L/mol) of tetrahydrofuran, 76.6 g (735 mmol, 2.93 eq) of 2,2-dimethoxypropane and 4.54 g (252 mmol, 1.00 eq) of water. The pH of the resulting liquid was controlled to 2 to 3 with the addition of 17.0 g (170 mmol, 0.677 eq) 98% concentrated sulfuric acid under ice cooling. Then, the liquid was stirred for 5 hours at room temperature. The thus-obtained reaction-terminated liquid was added to a mixed solution of an aqueous sodium hydrogencarbonate solution (prepared from 39.0 g (464 mmol, 1.85 eq) of sodium hydrogencarboante and 125 mL of water) and 250 mL of ethyl acetate under ice cooling and stirred for 30 minutes at the same temperature. The organic layer and the aqueous layer were recovered. The recovered aqueous layer was further extracted twice with 125 mL of ethyl acetate. The recovered organic layers were combined. The combined organic layer was concentrated under reduced pressure and subjected twice to azeotropic concentration with 50 mL under reduced pressure. With this, a crude product of hydrolysate of the following formula was obtained.

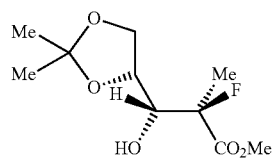

The ¹⁹F-NMR analysis results of the crude product were the same as those of Example 8.

The whole of the above-obtained crude product (regarded as 251 mmol) was mixed with 125 mL (0.5 L/mol) of methanol and 6.25 mL (75.0 mmol, 0.299 eq) of 12N hydrochloric acid. The resulting liquid was stirred for 18 hours at room temperature. The thus-obtained reaction-terminated liquid was concentrated under reduced pressure, subjected five times to azeotropic concentration with 50 mL of toluene under reduced pressure, and then, dried under vacuum. With this, a crude product of dihydroxylactone of the following formula was obtained.

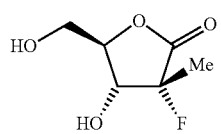

The ¹⁹F-NMR analysis results of the crude product were the same as those of Example 1.

The whole of the above-obtained crude product (regarded as 251 mmol) was mixed with 250 mL (1 L/mol) of acetonitrile and 49.1 g (621 mmol, 2.47 eq) of pyridine, followed by adding thereto 81.2 g (578 mmol, 2.30 eq) of benzoyl chloride under ice cooling. The resulting liquid was stirred for 2 hours at room temperature. To the thus-obtained reaction-terminated liquid, 125 mL of water was added under ice cooling. The reaction-terminated liquid was further stirred for 10 minutes at room temperature and extracted with 250 mL of ethyl acetate. The recovered organic layer was washed with 125 mL of 5% aqueous sodium hydrogencarbonate solution, further washed with 125 mL of 5% sodium chloride solution, concentrated under reduced pressure and dried under vacuum. There was thus obtained 140 g of a crude product of (2R)-2-fluoro-2-C-methyl-D-ribono-γ-lactone of the following formula.

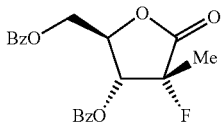

It was confirmed by ¹⁹F-NMR quantification analysis (internal standard method) of the crude product that the target compound of the above formula was contained in an amount of 184 mmol. The total yield from the 1,2-diol substrate was 73%. The $^{19}$F-NMR analysis results of the crude product were the same as those of Example 1.

The whole of, that is, 140 g (184 mmol) of the above-obtained crude product was recrystallized with a mixed solvent of 200 mL (1 vol) of ethyl acetate and 800 mL (6 vol) of n-heptane. The resulting crystalline substance was filtered out, washed with 150 mL of ice-cooled methanol and dried under vacuum. With this, 62.0 g (167 mmol) of the (2R)-2-fluoro-2-C-methyl-D-ribono-γ-lactone of the above formula was obtained as a purified product (pale yellow-white crystalline substance). The recovery was 91%. The gas chromatographic purity of the purified product was 100%.

Example 10

A pressure-proof reaction vessel of stainless steel (SUS) was charged with 250 mL (1 L/mol) of acetonitrile, 43.0 g (425 mmol, 1.71 eq) of triethylamine (Et$_3$N), 57.6 g (378 mmol, 1.52 eq) of 1,8-diazabicyclo[5.4.0]undec-7-ene (DBU) and 20.2 g (125 mmol, 0.502 eq) of triethylamine trihydrofluoride (Et$_3$N.3HF). The resulting liquid was stirred for 1 hour at room temperature, followed by adding thereto 58.4 g (249 mmol, 1.00 eq) of 1,2-diol of the following formula and blowing 44.0 g (431 mmol, 1.73 eq) of sulfuryl fluoride (SO$_2$F$_2$) at 0° C. from a cylinder into the reaction vessel.

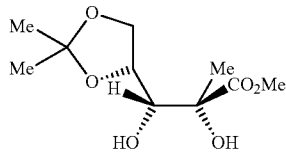

This liquid was stirred for 5 hours at 55° C. To the thus-obtained reaction-terminated liquid, an aqueous potassium carbonate solution (prepared from 45.1 g (326 mmol, 1.31 eq) of potassium carbonate and 125 mL of water) was added. After that, the reaction-terminated liquid was extracted with 250 mL of ethyl acetate. The recovered aqueous layer was again extracted with 125 mL of ethyl acetate. The recovered organic layers were combined. The combined organic layer was concentrated under reduced pressure and subjected three times to azeotropic concentration with 50 mL of toluene under reduced pressure. With this, a curde product of ring-opened fluorinated compound of the following formula was obtained (where Z$^+$ was proton, protonated triethylamine, protonated 1,8-diazabicyclo[5.4.0]undec-7-ene or potassium (derived from the aqueous potassium carbonate solution added for post-treatment operation)).

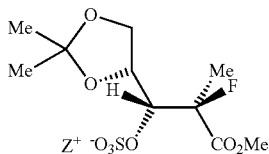

It was confirmed by $^{19}$F-NMR quantification analysis (internal standard method) of the crude product that the target compound of the above foimula was contained in an amount of 232 mmol. The yield was 93%. The $^{19}$F-NMR analysis results of the crude product were the same as those of Example 8.

The whole of the above-obtained crude product (for the sake of convenience, regarded as 249 mmol) was mixed with 125 mL (0.5 L/mol) of tetrahydrofuran, 78.7 g (756 mmol, 3.04 eq) of 2,2-dimethoxypropane and 4.52 g (251 mmol, 1.01 eq) of water. The pH of the resulting liquid was controlled to 2 to 3 with the addition of 14.8 g (148 mmol, 0.594 eq) of 98% concentrated sulfuric acid under ice cooling. Then, the liquid was stirred for 2 hours at room temperature. The thus-obtained reaction-terminated liquid was added to a mixed solution of an aqueous sodium hydrogencarbonate solution (prepared from 27.5 g (327 mmol, 1.31 eq) of sodium hydrogencarbonate and 125 mL of water) and 250 mL of ethyl acetate under ice cooling and stirred for 30 minutes at the same temperature. The organic layer and the aqueous layer were recovered. The recovered aqueous layer was further extracted twice with 125 mL of ethyl acetate. The recovered organic layers were combined. The combined organic layer was concentrated under reduced pressure and subjected twice to azeotropic concentration with 50 mL of toluene under reduced pressure. With this, a crude product of hydrolysate of the following formula was obtained.

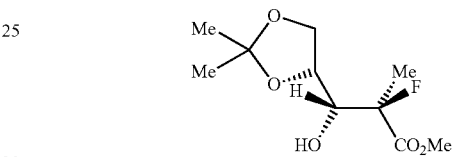

The $^{19}$F-NMR analysis results of the crude product were the same as those of Example 8.

The whole of the above-obtained crude product (for the sake of convenience, regarded as 249 mmol) was mixed with 125 mL (0.5 L/mol) of methanol and 6.25 mL (75.0 mmol, 0.301 eq) of 12N hydrochloric acid. The resulting liquid was stirred for 18 hours at room temperature. The thus-obtained reaction-terminated liquid was concentrated under reduced pressure, subjected five times to azeotropic concentration with 50 mL of toluene under reduced pressure, and then, dried under vacuum. With this, a crude product of dihydroxylactone of the following formula was obtained.

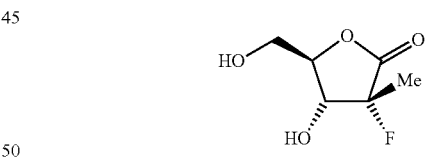

The $^{19}$F-NMR analysis results of the crude product were the same as those of Example 1.

The whole of the above-obtained crude product (for the sake of convenience, regarded as 249 mmol) was mixed with 250 mL (1 L/mol) of acetonitrile and 49.5 g (626 mmol, 2.51 eq) of pyridine, followed by adding thereto 79.9 g (568 mmol, 2.28 eq) of benzoyl chloride under ice cooling. The resulting liquid was stirred for 2 hours at room temperature. To the thus-obtained reaction-terminated liquid, 125 mL of water was added under ice cooling. The reaction-terminated liquid was further stirred for 10 minutes at room temperature and extracted with 250 mL of ethyl acetate. The recovered organic layer was washed with 125 mL of 5% aqueous sodium hydrogencarbonate solution, further washed with 125 mL of 5% sodium chloride solution, concentrated under reduced pressure and dried under vacuum. There was thus obtained 106 g of a crude product of (2R)-2-fluoro-2-C-methyl-D-ribono-γ-lactone of the following formula.

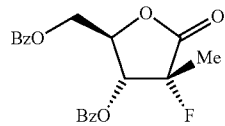

It was confirmed by $^{19}$F-NMR quantification analysis (internal standard method) of the crude product that the target compound of the above formula was contained in an amount of 193 mmol. The total yield from the 1,2-diol substrate was 78%. The $^{19}$F-NMR analysis results of the crude product were the same as those of Example 1.

The whole of, that is, 106 g (193 mmol) of the above-obtained crude product was recrystallized with a mixed solvent of 200 mL (2 vol) of ethyl acetate and 800 mL (8 vol) of n-heptane. The resulting crystalline substance was filtered out, washed with 110 mL of ice-cooled methanol and dried under vacuum. With this, 66.7 g (179 mmol) of the (2R)-2-fluoro-2-C-methyl-D-ribono-γ-lactone of the above formula was obtained as a purified product (pale yellow-white crystalline substance). The recovery was 93%. The gas chromatographic purity of the purified product was 99.6%.

INDUSTRIAL APPLICABILITY

The target compound of the present invention, that is, (2R)-2-fluoro-2-C-methyl-D-ribono-γ-lactone precursor is useful as an important intermediate for the synthesis of 2'-deoxy-2'-fluoro-2'-C-methylcytidine with antivirus activity.

Although the present invention has been described with reference to the above embodiments, various modifications and variations of the above embodiments can be made based on the knowledge of those skilled in the art without departing from the scope of the present invention.

The invention claimed is:

1. A method for producing a ring-opened fluorinated compound of the general formula [2], comprising: reacting a 1,2-diol of the general formula [1] with sulfuryl fluoride (SO$_2$F$_2$) in the presence of an organic base,

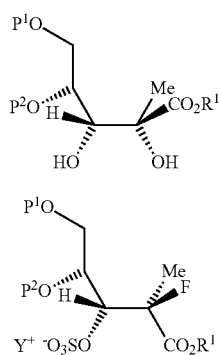

where Me represents a methyl group; R$^1$ represents an alkyl group or a substituted alkyl group; and P$^1$ and P$^2$ each independently represent a hydroxyl protecting group; and Y$^+$ represents a proton or a protonated organic base.

2. The method according to claim 1, wherein said reacting is performed in the additional presence of a fluoride ion source selected from the group consisting of hydrogen fluoride, a salt or complex of an organic base and hydrogen fluoride, a metal fluoride, a tetraalkylammonium fluoride, a complex of a tetraalkylammonium fluoride and hydrogen fluoride and a tris(dialkylamino)sulfonium trialkylsilyl difluoride; and wherein the ring-opened fluorinated compound is of the general formula [3],

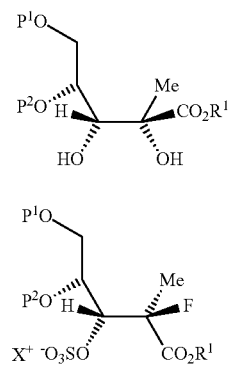

where Me represents a methyl group; R$^1$ represents an alkyl group or a substituted alkyl group; P$^1$ and P$^2$ each independently represent a hydroxyl protecting group; and X$^+$ represents a proton, a protonated organic base, a metal cation, a tetraalkylammonium or a tris(dialkylamino)sulfonium.

3. The method according to claim 1, wherein the 1,2-diol is of the general formula [4]; and wherein the ring-opened fluorinated compound is of the general formula [5],

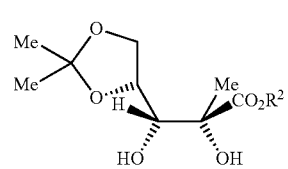

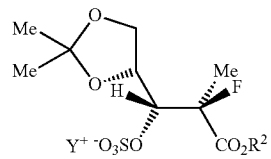

where Me represents a methyl group; R$^2$ represents a methyl group or an ethyl group; and Y$^+$ represents a proton or a protonated organic base.

4. The method according to claim 3, wherein said reacting is performed in the additional presence of a fluoride ion source selected from the group consisting of hydrogen fluoride, a salt or complex of an organic base and hydrogen fluoride, a metal fluoride, a tetraalkylammonium fluoride, a complex of a tetraalkylammonium fluoride and hydrogen fluoride and a tris(dialkylamino)sulfonium trialkylsilyl difluoride; and wherein the ring-opened fluorinated compound is of the general formula [6],

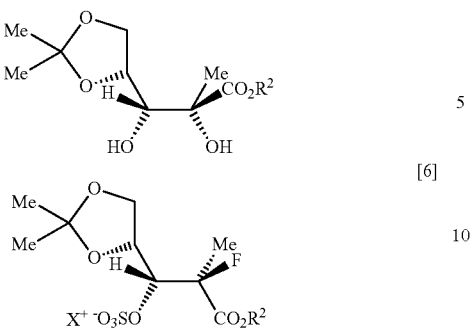
where Me represents a methyl group; $R^2$ represents a methyl group or an ethyl group; and $X^+$ represents a proton, a protonated organic base, a metal cation, a tetraalkylammonium or a tris(dialkylamino)sulfonium.
* * * * *